(12) United States Patent
Jewell et al.

(10) Patent No.: US 10,973,243 B2
(45) Date of Patent: Apr. 13, 2021

(54) ANIMAL FOOD PRODUCT FOR DENTAL EFFICACY, METHODS OF MANUFACTURE AND USE

(71) Applicant: Hill's Pet Nutrition, Inc., Topeka, KS (US)

(72) Inventors: Dennis Jewell, Lawrence, KS (US); Matthew Jackson, Topeka, KS (US); Christopher Waldy, Maple Hill, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 756 days.

(21) Appl. No.: 15/533,382

(22) PCT Filed: Dec. 19, 2014

(86) PCT No.: PCT/US2014/071740
§ 371 (c)(1),
(2) Date: Jun. 6, 2017

(87) PCT Pub. No.: WO2016/099571
PCT Pub. Date: Jun. 23, 2016

(65) Prior Publication Data
US 2017/0339978 A1 Nov. 30, 2017

(51) Int. Cl.
*A23K 10/30* (2016.01)
*A23K 20/147* (2016.01)
(Continued)

(52) U.S. Cl.
CPC .......... *A23K 10/30* (2016.05); *A23K 20/111* (2016.05); *A23K 20/142* (2016.05);
(Continued)

(58) Field of Classification Search
CPC ..... A23K 20/147; A23K 20/163; A23K 50/45
See application file for complete search history.

(56) References Cited

U.S. PATENT DOCUMENTS

| | | |
|---|---|---|
| 5,000,940 A | 3/1991 | Staples et al. |
| 5,296,209 A | 3/1994 | Simone et al. |

(Continued)

FOREIGN PATENT DOCUMENTS

| | | |
|---|---|---|
| CA | 1331447 | 8/1994 |
| EP | 0552897 | 7/1993 |

(Continued)

OTHER PUBLICATIONS

Essentials of Cell Biology, Unit 2: How Do Cells Decode Genetic Information into Functional Proteins?; available at: https://web.archive.org/web/20141110211857/https://www.nature.com/scitable/ebooks/essentials-of-cell-biology-14749010/122996920/, published on Nov. 10, 2014. (Year: 2014).*

(Continued)

*Primary Examiner* — Walter A Moore (57) ABSTRACT

The present disclosure is directed to an animal food product for promoting dental efficacy including a hydrolyzed protein including one or more amino groups, and a high amylopectin content starch including one or more reducing sugars; wherein the one or more amino groups in the hydrolyzed protein are covalently bonded to the one or more reducing sugars in the high amylopectin content starch. Methods of preparing the animal food product and using the animal food product to promote dental efficacy, such as teeth-cleaning efficacy in an animal are also provided.

20 Claims, 3 Drawing Sheets

Canine reference texture graph (51) Int. Cl.
- A23K 20/163 (2016.01)
- A23K 40/20 (2016.01)
- A23K 20/174 (2016.01)
- A23K 50/42 (2016.01)
- A23K 40/25 (2016.01)
- A23K 20/111 (2016.01)
- A23K 20/179 (2016.01)
- A23K 20/142 (2016.01)

(52) U.S. Cl.
CPC .......... *A23K 20/147* (2016.05); *A23K 20/163* (2016.05); *A23K 20/174* (2016.05); *A23K 20/179* (2016.05); *A23K 40/20* (2016.05); *A23K 40/25* (2016.05); *A23K 50/42* (2016.05)

(56) References Cited

U.S. PATENT DOCUMENTS

| | | | |
|---|---|---|---|
| 5,431,927 | A | 6/1995 | Hand et al. |
| 6,841,178 | B2 | 1/2005 | Cupp et al. |
| 8,168,161 | B2 | 5/2012 | Scherl et al. |
| 2001/0002272 | A1* | 5/2001 | Brunner .................. A23K 40/30 426/656 |
| 2003/0104102 | A1* | 6/2003 | Nelles .................... A23L 27/201 426/535 |
| 2003/0228349 | A1* | 12/2003 | Singh ...................... A23K 10/14 424/442 |
| 2005/0084563 | A1 | 4/2005 | Cupp et al. |
| 2006/0110501 | A1 | 5/2006 | Axelrod |
| 2007/0087108 | A1* | 4/2007 | Wadsworth .......... A23K 20/163 426/635 |
| 2008/0206405 | A1 | 8/2008 | Axelrod et al. |
| 2009/0054301 | A1* | 2/2009 | Dierking .................. A23J 3/30 514/1.1 |
| 2009/0263565 | A1* | 10/2009 | Ryder ...................... A23J 3/26 426/656 |
| 2012/0021114 | A1* | 1/2012 | Ferriss .................. A23C 9/1544 426/578 |
| 2012/0288533 | A1* | 11/2012 | Livney ...................... A23L 2/52 424/400 |
| 2012/0288590 | A1* | 11/2012 | Soane ...................... A23L 17/75 426/92 |
| 2013/0101648 | A1 | 4/2013 | Axelrod et al. |
| 2013/0264731 | A1* | 10/2013 | Baier .................. D01D 5/0038 264/10 |
| 2013/0273206 | A1 | 10/2013 | Moulton |
| 2013/0309357 | A1* | 11/2013 | Mercenier .............. A23K 10/18 426/61 |
| 2013/0309384 | A1* | 11/2013 | Villagran ............... A23K 40/20 426/560 |
| 2014/0227783 | A1* | 8/2014 | Masutani .............. C12N 5/0062 435/397 |
| 2014/0314819 | A1 | 10/2014 | Scherl et al. |
| 2015/0328250 | A1 | 11/2015 | Montelongo et al. |

FOREIGN PATENT DOCUMENTS

| | | | |
|---|---|---|---|
| EP | 0719783 | 10/1999 | |
| EP | 1440622 | 7/2004 | |
| EP | 1800545 | 6/2007 | |
| WO | WO 2012/156674 | 11/2012 | |
| WO | WO-2013050406 A1 * | 4/2013 | ............. A23K 10/12 |
| WO | WO 2013/089842 | 6/2013 | |
| WO | WO 2014/015513 | 1/2014 | |
| WO | WO 2014/098823 | 6/2014 | |

OTHER PUBLICATIONS

International Search Report and Written Opinion of the International Searching Authority in International Application No. PCT/US2014/071740, dated May 4, 2015.

* cited by examiner

ANIMAL FOOD PRODUCT FOR DENTAL EFFICACY, METHODS OF MANUFACTURE AND USE

BACKGROUND

Many animals, particularly companion animals such as cats and dogs, suffer from dental health problems. A primary factor in the development of these problems is the formation of plaque on the surface of the teeth. Plaque contains bacteria and other components that adhere to the surface of the teeth, accumulating both above and below the gum line leading to inflammation, gingivitis, and/or malodors in the dental cavity.

Contributing to the problem is the formation of tartar or dental calculus (mineralized plaque). Dental calculus forms on the tooth surface at or above the gum line and serves as a substrate for additional accumulation of plaque. Apart from causing gum irritation and eventually periodontal disease if left untreated, the calculus has an unsightly appearance.

Animals in the wild are less susceptible than pets, for example, to the formation of plaque and calculus due to the types of food they eat. Many of these natural foods mechanically abrade plaque and calculus from the teeth. However, pets, farm animals and zoo animals, for example, are often fed commercially available foods. While commercially available foods are usually much better for an animal from a nutritional point of view, they generally do not subject the teeth of the animals to abrasive forces sufficient to clean the teeth. Even dried kibble is able to abrade the teeth only to a very limited extent. This is because dried kibble typically crumbles almost immediately when chewed by the animal.

There have been various attempts to deal with this problem. One approach has been to incorporate oral care agents into certain animal foods. For example, baked dog biscuits that contain vegetable fibers for abrading the teeth of a dog are known in the art. However, the biscuits almost immediately crumble upon being bitten. Hence, the dog is unable to chew the product in a manner that is adequate to clean teeth. Accordingly, little abrasion occurs and the dental efficacy (e.g. the teeth-cleaning efficacy), of the product is reduced. In addition, such products are not readily suitable for many varieties of animals such as cats, for example.

A dried animal food product has also been formulated that contains aligned fibers. When chewed, the product fractures along striations rather than crumbles. Accordingly, the product is able to be in contact with the animal's teeth for a longer period of time, and consequently, the abrasive effect of the product is enhanced. However, the product must be produced using a specially coated die which permits laminar flow conditions within the die. The laminar flow conditions are reported to cause alignment of the fibers within the product leading to the striated fracturing of the product when bitten. The use of the special die, however, may unnecessarily complicate production of the product and increase the cost of production. Accordingly, there remains a desire in the art for animal food products having dental efficacy, which may be simply and cheaply manufactured and readily used in a variety of food items.

BRIEF SUMMARY

The present disclosure is directed to an animal food product for promoting dental efficacy including: a hydrolyzed protein including one or more amino groups, and a high amylopectin content starch including one or more reducing sugars; wherein the one or more amino groups in the hydrolyzed protein are covalently bonded to the one or more reducing sugars in the high amylopectin content starch.

The present disclosure also provides a method of preparing an animal food product for promoting dental efficacy, the method including: preparing a food mixture including a high amylopectin content starch and a hydrolyzed protein, wherein the high amylopectin content starch includes one or more reducing sugars and the hydrolyzed protein includes one or more amino groups, working the food mixture under mechanical pressure and heat sufficient to convert the mixture to a flowable mass and discharging the flowable mass through a die to form an extrudate including the high amylopectin content starch and the hydrolyzed protein, wherein the one or more reducing sugars in the high amylopectin content starch forms a covalent bond with the one or more amino groups in the hydrolyzed protein.

Also provided herein is a method of preparing an animal food product for promoting dental efficacy including: preparing a food mixture comprising a high amylopectin content starch and a hydrolyzed protein, wherein the high amylopectin content starch includes one or more reducing sugars and the hydrolyzed protein includes one or more amino groups, placing the food mixture into a mold suitable for the animal food; exposing the food mixture in the mold to a dry heat processing, wherein the one or more reducing sugars in the high amylopectin content starch forms a covalent bond with the one or more amino groups in the hydrolyzed protein.

The present disclosure also provides a method of promoting dental efficacy in an animal, the method including: feeding an animal food product to an animal, wherein the animal food product includes a high amylopectin content starch including one or more reducing sugars, and a hydrolyzed protein, including one or more amino groups; wherein the one or more reducing sugars in the high amylopectin content starch is covalently bonded to the one or more amino groups in the hydrolyzed protein.

Further areas of applicability of the present disclosure will become apparent from the detailed description provided hereinafter. It should be understood that the detailed description and specific examples, while indicating the typical embodiments of the disclosure, are intended for purposes of illustration only and are not intended to limit the scope of the disclosure.

BRIEF DESCRIPTION OF THE DRAWINGS

The present invention will become more fully understood from the detailed description and the accompanying drawings, wherein.

DETAILED DESCRIPTION

The following description of the typical embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The inventors surprisingly found that the addition of hydrolyzed protein to a conventional animal food product significantly improved its texture in a manner that causes the animal food product to be less prone to crumbling or breakage upon being bitten. Further, the texture of the modified food product was more elastic than conventional products, indicating that an animal's teeth would be able to more deeply penetrate the food product, consequently allowing for a longer contact time between the food product and an animal's teeth, which would improve the product's cleaning effect on an animal's oral surfaces, such as teeth surfaces. Unexpectedly, the inventors additionally recognized that these beneficial properties could be even further enhanced by combining the hydrolyzed protein with a high amylopectin content starch. Moreover, the inventors recognized that the addition of cellulose could further increase the kilogram-force (kgf) required for breakage of the animal food product without compromising the elasticity of the product. Accordingly, the present animal food product may be efficaciously used to promote the oral health of an animal, for example, by improving the dental cleaning effect of the product.

Compositions

The present disclosure provides an animal food product for dental efficacy. As used herein, the phrase "animal food product" refers to a food product that is formulated for an animal. The term "animal" as used herein refers to non-human animals, such as mammals and is particularly applicable to companion animals. The term "companion animal" as used herein encompasses any animal that lives in close association with humans and is not limited to cats and dogs. Moreover, it is contemplated herein that the term animal may also encompass any animal whose diet may be controlled by humans and which may benefit from feeding the formulations disclosed herein. These animals may include, e.g., domesticated farm animals (e.g. cattle, horses, swine, etc.) as well as undomesticated animals held in captivity, e.g. in zoological parks and the like.

Mammalian animals include, for example, non-human primates, such as monkeys and chimpanzees, farm animals such as goats, sheep, swine, horses, cattle, etc., and wild and zoo animals, such as wolves, bears, deer, giraffes, elephants, etc. The term animal further encompasses animals in various stages in life, including lactation, weaning, growth, adult, senior, and geriatric. In specific embodiments, the animal is an adult, senior, or geriatric animal, and particularly, an adult animal. The present animal food product may be formulated for one or more of these specific types of animals.

The term "cat" includes those cats that are companion animals known as domestic cats or house cats. The term cat is synonymous with the term feline.

The term "dog" includes those dogs that are companion animals such as *Canis familiaris*, working dogs and the like. The term dog is synonymous with the term canine.

As used herein, the term "food" encompasses a product or composition that is intended for ingestion by an animal. As described herein, a food may be nutritionally complete or nutritionally incomplete. The term "food" includes any food, for example, a dried food such as a kibble, snack, food supplement, treat, or toy (e.g., chewable and/or consumable toys).

The term "supplement" as used herein means a product that is intended to be ingested in addition to the normal animal diet.

The term "treat" (or "biscuit") as used herein refers to any food item that is designed to be fed to an animal, typically at a non-meal time, by the owner to help, promote or sustain a bonding process between a pet and its owner. Examples of treats for dogs are bones.

The term "toy" encompasses both partially consumable toys (e.g., toys comprising plastic components) and fully consumable toys (e.g., rawhides and various artificial bones). It should be further recognized that this disclosure contemplates toys for companion, farm, and zoo animal use, and particularly for canine or feline use.

The terms "treat" and "toy" can be considered interchangeable for the purposes of this specification. However, in general, a treat is fully edible and a toy in accordance with the present disclosure has an edible coating.

In some embodiments, the present animal food product comprises hydrolyzed protein. As used herein, the phrase "hydrolyzed protein" refers to the chemical reaction of a protein with water to produce two or more smaller molecules, e.g. polypeptides. The term "polypeptide" as used herein describes linear molecular chains of amino acids. In some embodiments, hydrolysis of the protein may be catalyzed by acids, alkalis, or enzymes. "Hydrolysis" is the underlying reaction in the conversion of proteins to their hydrolysates.

In certain embodiments, the animal food product comprises a hydrolysate in which about 50% to about 95% of the polypeptides have a molecular weight below about 20,000 daltons, below about 15,000 daltons, below about 10,000 daltons, below or about 8,000 daltons, or below or about 5,000 daltons. Yet even more typically, the animal food product comprises a hydrolysate in which at least about 50%, more typically at least about 60%, even more typically at least about 75% or even more typically at least about 95% of the polypeptides have a molecular weight ranging from about 5,000 to about 20,000 daltons, more typically ranging from about 6,000 to about 15,000 daltons and even more typically ranging from about 8,000 to about 10,000 daltons.

In some embodiments, the animal food product comprising a protein hydrolysate having a molar mass distribution ranging from 8,000 to 10,000 daltons, for example, may be obtained by subjecting the protein hydrolysate to well-known filtering procedures or any other procedure known in the art for removing peptides, amino acids, and/or other proteinaceous material having a molar mass of less than 8000 daltons or greater than 10,000 daltons. The term "molar mass distribution" when used in reference to a hydrolyzed protein or protein hydrolysate pertains to the molar mass of each polypeptide present in the protein hydrolysate. For example, a protein hydrolysate having a molar mass distribution of greater than 8000 daltons means that each polypeptide included in the protein hydrolysate has a molar mass of at least about 8000 daltons.

In various embodiments, the protein hydrolysate may be an animal protein hydrolysate. An animal protein hydrolysate can be, without limitation, a hydrolysate of a protein obtained from the tissue of an animal, such as a tissue from a cow, a fish, an invertebrate, a reptile, an amphibian, or a bird, e.g., hydrolyzed chicken liver and/or heart.

In various embodiments, the protein hydrolysate may be a plant protein hydrolysate. A plant hydrolysate includes but is not limited to a hydrolysate of protein obtained from an edible tissue of a plant, e.g., a grain, a fruit, a root, a tuber, a stem or a leaf.

In some embodiments, the animal food product of the present disclosure includes an amount of hydrolyzed protein ranging from about 20 wt % to about 60 wt %, more typically ranging from about 35 wt % to 40 wt %. Even more typically, the animal food product of the present disclosure includes an amount of hydrolyzed protein ranging from about 37 wt % to 39 wt %.

In some embodiments, the animal food product of the present disclosure includes a starch having a high amylopectin content. As is known in the art, the starch of plants commonly contains two types of glucose polymer, amylopectin and amylose. Amylopectin is a very long chain molecule, having a molecular weight greater than 1,000,000 daltons. It is a relatively highly branched homopolymer of α-D-glucopyranoside consisting of side chains of numerous D-(+)-glucose units. Each unit of glucose is joined by an α-glycoside linkage to C-4 of the next unit. Amylopectin has a branched structure consisting of numerous chains of about 20 to about 25 glucose units each. One end of each of these shorter chains is joined through a C-1 on a first chain to a C-6 on a second chain, as shown below:

rice, waxy barley, waxy sorghum, waxy wheat and waxy varieties of root and tuber starches such as those of tapioca and potato. Many waxy starches are commercially available, e.g., Eliane™ 100 waxy potato starch, from the AVEBE Company of Veendam, Netherlands.

In some embodiments, the high amylopectin content starch of the present disclosure contains reducing sugars. As used herein, a reducing sugar is any sugar that either has an aldehyde group or is capable of forming one in solution through isomerism. In glucose polymers, such as starch and starch-derivatives like glucose syrup, maltodextrin and dextrin, the macromolecule begins with a reducing sugar, a free aldehyde.

In some embodiments, the amount of reducing sugars in the high amylopectin content starch may be increased by treating the high amylopectin content starch with enzymes, such as amylase, acid or heat, resulting in partial hydrolysis of the starch. In other embodiments, reducing sugars may be formed during storage from seeds or tubers of plants, such as potatoes, before processing into starch. For example, as is known in the art, potatoes used to obtain starch may be stored at cold temperatures, e.g. around 4° C. to increase the amount of reducing sugars.

In some embodiments, the high amylopectin starch contains an amount of reducing sugars ranging from 0.5% to 20% dry weight, about 0.5% to 10% dry weight, more typically about 0.5% to 5% dry weight, yet more typically 0.5% to 4%, and even more typically about 0.5% to 3.5% dry weight. The reducing sugar content of the high amylopectin starch in accordance with the present disclosure can be determined by any method known to those skilled in the art, e.g., by methods for reducing cuprotartaric liquors or by colorimetric methods with dinitrosalicylic acid.

As used herein, the phrase "high amylopectin content" in reference to starch means that the starch has an amylopectin content of at least about 85%, more typically at least about 90%, even more typically at least about 95%, and even more typically at least about 98%. In some embodiments, the high amylopectin content starch contains 99% or more of amylopectin. In some embodiments, pure amylopectin is used with the present animal food product.

The high amylopectin content starches for use with the present animal food product may be obtained from or originate from plants such as wheat, corn, barley, triticale, sorghum or rice; the starches of tubers such as potato or cassava; the starches of leguminous plants such as peas, soybeans or beans or any mixtures of these starches. More typically, waxy starches are used, e.g., waxy maize, waxy Without being limited by theory, the reducing sugars in the high amylopectin content starch of the present disclosure may be susceptible to the Maillard reaction (a chemical reaction between an amino acid and a reducing sugar, generally requiring heat). Accordingly, when the high amylopectin content starch comprising the reducing sugars are combined with hydrolyzed protein under suitable conditions, such as during baking, covalent bonds form between the amino groups of the polypeptides, the free aldehyde present in the amylopectin and/or the reducing sugars in the starch derivatives contained within the present high amylopectin content starch resulting in polymers, which provide the structural features contributing to the texture of the present animal food product, which is useful for promoting dental efficacy, such as oral surface cleaning efficacy.

In some embodiments, the animal food product of the present disclosure includes between 2 wt % to 75 wt %, such as 7 wt % to 60 wt %, or such as 30 wt % to 59 wt % of high amylopectin starch.

In some embodiments, the present animal food product further includes a common starch, such as common corn starch. As used herein, the phrase "common starch" refers to a starch having an amylose content ranging from about 16 wt % to about 70 wt %. In some embodiments, the amount of common starch included in the animal food product ranges from about 25 wt. % to about 60 wt %.

In some embodiments, the composition of the present disclosure further includes fiber. Examples of fibers that may be used with the instant animal food product include soy fiber, rice hull fiber, pea hull fiber, oat hull fiber, barley hull fiber, sugar beet fiber, wheat bran fiber and pure cellulose. Dietary fiber sources include cell wall polysaccharides (e.g., cellulose, hemicelluloses, pectins) and non-cell wall polysaccharides (e.g., guar, locust bean gums, gum arabic, gum karaya, tragacanth gums, agar, alginates and carrageenan).

In some embodiments, the amount of fiber in the present composition is between about 1.0 wt % and about 10.0 wt %, more typically, about 1 wt % to about 7 wt %, more typically from about 1 wt % to about 5 wt %, even more typically about 4 wt % or less. In some embodiments, the fiber in the present composition is pure cellulose, such as powdered cellulose, which is commercially available.

In some embodiments, the animal food product of the present disclosure further comprises fats. Exemplary fats, such as vegetable oils, which may be used with the present animal food product include, but are not limited to, corn oil, olive oil, safflower oil, peanut oil, palm oil, rapeseed oil, soybean oil, cottonseed oil, coconut oil, canola oil, etc. Animal fats include but are not limited to beef fat, pork fat, poultry fat, and fish oils.

In other embodiments, the animal food product of the present disclosure further comprises an antioxidant. For example, the animal food product may include vitamin C, vitamin E, vitamin A, lipoic acid, astaxanthin, beta-carotene, L-carnitine, coenzyme Q10, glutathione, lycopene, lutein, N-acetylcysteine, soy isoflavones, S-adenosylmethionine, taurine, tocotrienols, spinach, tomato, citrus fruit, grape, carrot, broccoli, green tea, *Ginkgo biloba*, corn gluten meal, rice bran, algae, curcumin, marine oil, fruits, vegetables, yeast, carotenoids, flavonoids, polyphenols, and mixtures thereof.

In certain embodiments, the antioxidant-comprising animal food product can comprise vitamin E, vitamin C, or both vitamin E and vitamin C. In one aspect of this embodiment, the vitamin E content of a composition can be at least about 100 ppm, illustratively about 100 to about 5000 ppm, about 250 to about 2500 ppm, or about 500 to about 1500 ppm. In another aspect of this embodiment, the vitamin C content of a composition can be at least about 10 ppm, illustratively about 10 ppm to about 10,000 ppm, or about 20 to about 2000 ppm, or about 25 to about 500 ppm.

In some embodiments, the animal food product of the present disclosure further comprises minerals, additional vitamins and other additives. Such additional ingredients include but are not limited to iodized salt, L-lysine, choline chloride, potassium chloride, niacin, thiamine mononitrate, calcium pantothenate, biotin, vitamin $B_{12}$ supplement, pyridoxine hydrochloride, riboflavin, folic acid, vitamin $D_3$ supplement), minerals (e.g., ferrous sulfate, zinc oxide, copper sulfate, manganous oxide, calcium iodate, sodium selenite), L-carnitine, preserved with mixed tocopherols and citric acid, phosphoric acid, beta-carotene, rosemary extract and coloring, e.g. caramel coloring.

In certain embodiments, the animal food product of the present disclosure may further comprise at least one of a commercial liquid palatant enhancer or other flavor composition to create a novel flavor palatant which can then be included within or topically applied to the animal food product. Suitable commercial liquid palatant enhancers for use with the present animal food product can include any known or commercially available liquid palatant enhancers commercially available and known to those of skill in the art. In one illustrative aspect, a kibble, treat, or toy can be coated with a composition comprising the hydrolyzed protein, high amylopectin content starch and optionally cellulose as described herein and a carrier, wherein the carrier comprises protease-treated minced animal by-product, amino acids, one or more reducing sugars and thiamin.

In some embodiments, the animal food product of the present disclosure is a nutritionally complete food. A "nutritionally-complete", "nutritionally-balanced" or "complete and nutritionally-balanced food" is one that contains all known required nutrients for the intended recipient or consumer of the food, in appropriate amounts and proportions based, for example, on recommendations of recognized or competent authorities in the field of animal nutrition. Such foods are therefore capable of serving as a sole source of dietary intake to maintain life or promote production, without the addition of supplemental nutritional sources.

In some embodiments, a nutritionally complete food comprises the high amylopectin starch as described herein and optionally other carbohydrates in an amount ranging from 20 wt % to 70 wt %, hydrolyzed protein as described herein and, optionally, other proteins in an amount ranging from about 10% to about 50% protein, crude fiber in an amount of about 4% to about 20%, and fat in an amount ranging from about 4% to about 25%. In some embodiments, the nutritionally complete food also comprises the vitamins, minerals, antioxidants and other additives described herein.

In some embodiments, the animal food product is formed into a kibble. As used herein, "kibble" refers to particulate chunks or pieces or pellets typically formed by either a pelleting or extrusion process. In some embodiments, the animal food products of the instant disclosure, such as kibble, have a moisture level less than or equal to 15%, by weight of the food product, more typically 6 wt % to 9 wt % or even more typically 7 wt % to 8 wt %.

The dimensions of the kibble may include any desired dimensions. In some embodiments, the kibble of the present disclosure is 1-6 cm in all dimensions, such as 1-4 cm and such as 1-3 cm. In some embodiments, the width of the kibble is ranges from 3.0 to 3.5 cm, the length of the kibble ranges from about 1.7 cm to about 2.7 cm and thickness ranges from 1.7 to 2.5 cm. The kibble may be shaped as desired, e.g., a tube, a triangle, a sphere, a cross or a disc.

In other embodiments, the length, which may be the longest dimension of the animal food product, is greater than 0.75 cm, such as 0.75 to 20 cm, such as 2 to 18 cm, or such as 6 to 16 cm. In some embodiments, the width is in a range of 0.5 to 10 cm, such as 0.75 to 8 cm, such as 1.0 to 7 cm, or such as 2.0 to 6 cm. In some embodiments, the depth may range from 0.5 to 10 cm, such as 0.75 to 8 cm, such as 1.0 to 7 cm, or such as 2.0 to 6 cm. In some embodiments, the cross sectional areas may range from 3.0 to 18.0 $cm^2$ such as 3.2 $cm^2$, such as 4.3 $cm^2$, or such as 6.5 $cm^2$, or, for example, about 12.9 $cm^2$.

In some embodiments, the animal food product is nutritionally incomplete. In these embodiments, while the animal food product may contribute to the nutritional and colorific content of the animal's diet, the composition is not an independent source of the animal's complete daily nutritional and colorific needs. Typically, in this embodiment, the animal food product is formed as a treat, snack or a coating for a toy, typically chewable and consumable toys.

In some embodiments, the animal food product of the present disclosure has a texture such that a probe, having a contact area of about 6.80 mm wide×1.00, for example, and operated at a speed of about 5 mm/s, for example, penetrates into the formed dried pet food product, such as a kibble, for a distance of at least about 29%, more typically at least about 40%, such as at least about 50% or more typically at least about 70% of the thickness of the formed dried pet food, prior to breaking or crumbling of the formed dried pet food.

For example, for a kibble having a depth of about 30 mm, the probe may penetrate a distance of at least about 10 mm, more typically at least about 12 mm or more typically about 15 mm, prior to breaking of the dried animal food product. As a further example, the kibble has a thickness of about 17 mm and the probe penetrates a distance of at least about 5 mm, more typically about 8 mm, even more typically about 13 mm.

As used herein, the term "texture" encompasses the elasticity and hardness of an animal food product, which are reflected in the product's resistance to breaking or crumbling and the distance the probe is able to travel. Large penetration distance numbers or percentages are indicative of more elastic products, e.g., products that are more resistant to breaking or crumbling and that contact and clean the teeth longer when chewed.

In some embodiments, the time period for the probe as described above to penetrate the animal food product until the product breaks is at least 1.0 second, more typically, at least 1.5 seconds, yet more typically 2.5 seconds, even more typically at least 2.7 seconds and yet even more typically, at least 3.0 seconds. In some embodiments, the time period for the probe as described above to penetrate the animal food product is the same as the "contact time." Contact time may be determined as described in the Examples.

In some embodiments, the present animal food product has a hardness ranging from 3 to 16 kg-force, such as 3-4 kg-force such as 7-14 kg-force and such as, 8-11 kg-force. As used herein "hardness" refers to the peak force of a first compression of a product and provides information about the force needed to produce breakage or crumbling of the product.

Methods

In particular embodiments, the animal food product, and particularly the nutritionally-complete animal food products of the present disclosure, can be prepared in a dry form using conventional processes. In one contemplated embodiment, dry ingredients, including, for example, high amylopectin starch, hydrolyzed proteins, and optionally, cellulose in the form of powdered cellulose, for example, are ground and mixed together. Moist or liquid ingredients, including fats, oils, water, etc., are then added to and mixed with the dry mix. The mixture is then processed into kibbles or similar dry pieces. Kibble may be formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which can include, for example, flavors, fats, oils, powders, and the like. In some embodiments, kibble also can be made from a dough using a baking process, rather than extrusion, wherein the dough is placed into a mold before dry-heat processing.

Treats of the present invention can be prepared by, for example, an extrusion or baking process similar to those described above for dry food. Other processes also can be used to either apply a coating comprising the animal food product as described herein on the exterior of existing treat forms, or injecting the copolymer into an existing treat form.

In another embodiment, the present animal food product is formed into a coating and coated onto a surface of a toy, for example, an artificial bone for a dog or on a surface of a component of the toy. In some embodiments, the present animal food product can be incorporated partially or fully throughout the toy.

The present disclosure is also directed to a method of promoting dental efficacy in an animal. As used herein, the phrase "dental efficacy" encompasses preventing, curing, reversing, attenuating, alleviating, ameliorating, minimizing, suppressing or halting the deleterious effects of one or more dental conditions in an animal. Among other things, dental efficacy includes the ability or capacity to clean the teeth of an animal. The phrase "dental conditions" include but are not limited to plaque, tartar, stains, halitosis, gingivitis, periodontitis, and combinations thereof.

The present methods for promoting dental efficacy comprise feeding an animal the animal food product described herein. The methods of the present disclosure contemplate feeding the animal food product of the present disclosure in any desirable from including as a food, such as a kibble, supplements, treats, snacks and toys and the like.

In various embodiments, the present animal food product can be fed to the animal as a component of its food intake. The food intake of the animal can meet its ordinary nutritional requirements, which a skilled artisan can readily determine based upon the animal's species, age, sex, weight, and other factors.

EXAMPLES

Example 1

Kibble products were prepared that contained 1) hydrolyzed protein, 2) hydrolyzed protein and high amylopectin content starch and 3) hydrolyzed protein, high amylopectin content starch and cellulose as shown in Table 1, below. The products were formulated as canine treats. For each of the products (T1-T13) dry mixes were prepared using the ingredients described in Table 1. The ingredients were blended in a 3000 lb ribbon mixer. Kibble was extruded using a 115 mm single screw extruder with two die holes using a low shear screw profile. Coconut oil was topically sprayed with pressure onto each kibble product as it mixed in a 300 lb mixer. The downspout temperature, downspout moisture content, extrudate temperature and specific mechanical energy (SME) observed during preparation of the kibble products are shown in Table 2.

TABLE 1

KIBBLE INGREDIENTS

| Test ID | Corn starch common (wt %) | Eliane™ 100 Potato Starch (waxy potato) (wt %) | Hydrolyzed chicken liver & heart (wt %) | Poultry Meal Regular Ash (wt %) | Powdered Cellulose (wt %) | Coconut oil (wt %) |
|---|---|---|---|---|---|---|
| T1 | 59.00 | 0.00 | 39.00 | 0.00 | 0.00 | 2.00 |
| T2 | 55.31 | 3.69 | 39.00 | 0.00 | 0.00 | 2.00 |
| T3 | 51.63 | 7.38 | 39.00 | 0.00 | 0.00 | 2.00 |
| T4 | 44.25 | 14.75 | 39.00 | 0.00 | 0.00 | 2.00 |
| T5 | 29.50 | 29.50 | 39.00 | 0.00 | 0.00 | 2.00 |
| T6 | 55.00 | 0.00 | 39.00 | 0.00 | 4.00 | 2.00 |
| T7 | 51.56 | 3.44 | 39.00 | 0.00 | 4.00 | 2.00 |
| T8 | 48.13 | 6.88 | 39.00 | 0.00 | 4.00 | 2.00 |
| T9 | 41.25 | 13.75 | 39.00 | 0.00 | 4.00 | 2.00 |
| T10 | 27.50 | 27.50 | 39.00 | 0.00 | 4.00 | 2.00 |
| T11 | 0.00 | 59.00 | 39.00 | 0.00 | 0.00 | 2.00 |
| T12 | 0.00 | 55.00 | 39.00 | 0.00 | 4.00 | 2.00 |
| T13 | 0.00 | 59.00 | 0.00 | 39.00 | 0.00 | 2.00 |

TABLE 2

PROCESSING DATA

| Test ID | Downspout Temperature (° C.) | Downspout Moisture Content (%) | Extrudate Temperature (° C.) | Specific Mechanical Energy (SME) (w-hr/kg) |
|---|---|---|---|---|
| T1 | 83.4 | 23.3 | 122 | 36 |
| T2 | 78.8 | 21.8 | 124.6 | 40 |
| T3 | 78.6 | 21.9 | 122.6 | 39 |
| T4 | 79.2 | 19.1 | 131.1 | 42 |
| T5 | 79.4 | 19.3 | 124.8 | 37 |
| T6 | 77.2 | 22.8 | 117.7 | 47 |
| T7 | 79.7 | 21.6 | 126.6 | 38 |
| T8 | 79.8 | 21.6 | 124.7 | 37 |
| T9 | 80 | 21.7 | 122.9 | 37 |
| T10 | 80.9 | 21.9 | 118.7 | 33 |
| T11 | 58.1 | 15.3 | 114.7 | 49 |
| T12 | 58.1 | 18.1 | 116.4 | 49 |
| T13 | 79.5 | 22.6 | 121.1 | 37 |

As shown in Table 3, below, the moisture content of the formed kibbles ranged from 7.16% to 8.31%. Protein, fat and ash content ranged from 24.01%-27.48%, 6.30%-10.69% and 2.11%-4.84%, respectively.

TABLE 3

| Test ID | Moisture (%) | Protein (%) | Fat (%) | Ash (%) |
|---|---|---|---|---|
| T1 | 7.45 | 24.04 | 10.69 | 2.13 |
| T2 | 7.50 | 24.03 | 10.69 | 2.12 |
| T3 | 7.55 | 24.03 | 10.69 | 2.12 |
| T4 | 7.64 | 24.03 | 10.69 | 2.12 |
| T5 | 7.84 | 24.02 | 10.68 | 2.11 |
| T6 | 7.16 | 24.04 | 10.69 | 2.14 |
| T7 | 7.20 | 24.04 | 10.69 | 2.13 |
| T8 | 7.24 | 24.04 | 10.69 | 2.13 |
| T9 | 7.33 | 24.04 | 10.69 | 2.13 |
| T10 | 7.51 | 24.03 | 10.68 | 2.12 |
| T11 | 8.22 | 24.01 | 10.67 | 2.10 |
| T12 | 7.87 | 24.02 | 10.67 | 2.11 |
| T13 | 8.31 | 27.48 | 6.30 | 4.84 |

The kibbles obtained as described above were subjected to texture analysis using a Texture Analyzer. The Texture Analyzer was fitted with a probe having a length of about 10 cm. The contact area of the probe was 6.80 mm wide×1.00 mm thick. The Texture Analyzer was operated at a speed of about 5 mm/s.

Each piece of kibble to be tested was placed on a base under the probe. The probe was moved downwardly and into the piece. The distance of penetration of the probe into the piece, the compression force and the time are recorded at a rate of 200 recordings per second. Breakage of the piece is determined upon a sharp fall off of the compression force. The distance of penetration, the compression force and the time are recorded at the moment of breakage.

The force (g) to breakage for each formulation of kibble, T1-T13, was determined. In addition, twenty replicates were tested for each formulation to determine the average force to breakage, standard deviation (SD) and coefficient of variation (CV). The time the probe was in contact with the kibble prior to breakage (contact time) was established by plotting the force (g) versus time.

Figure 1:
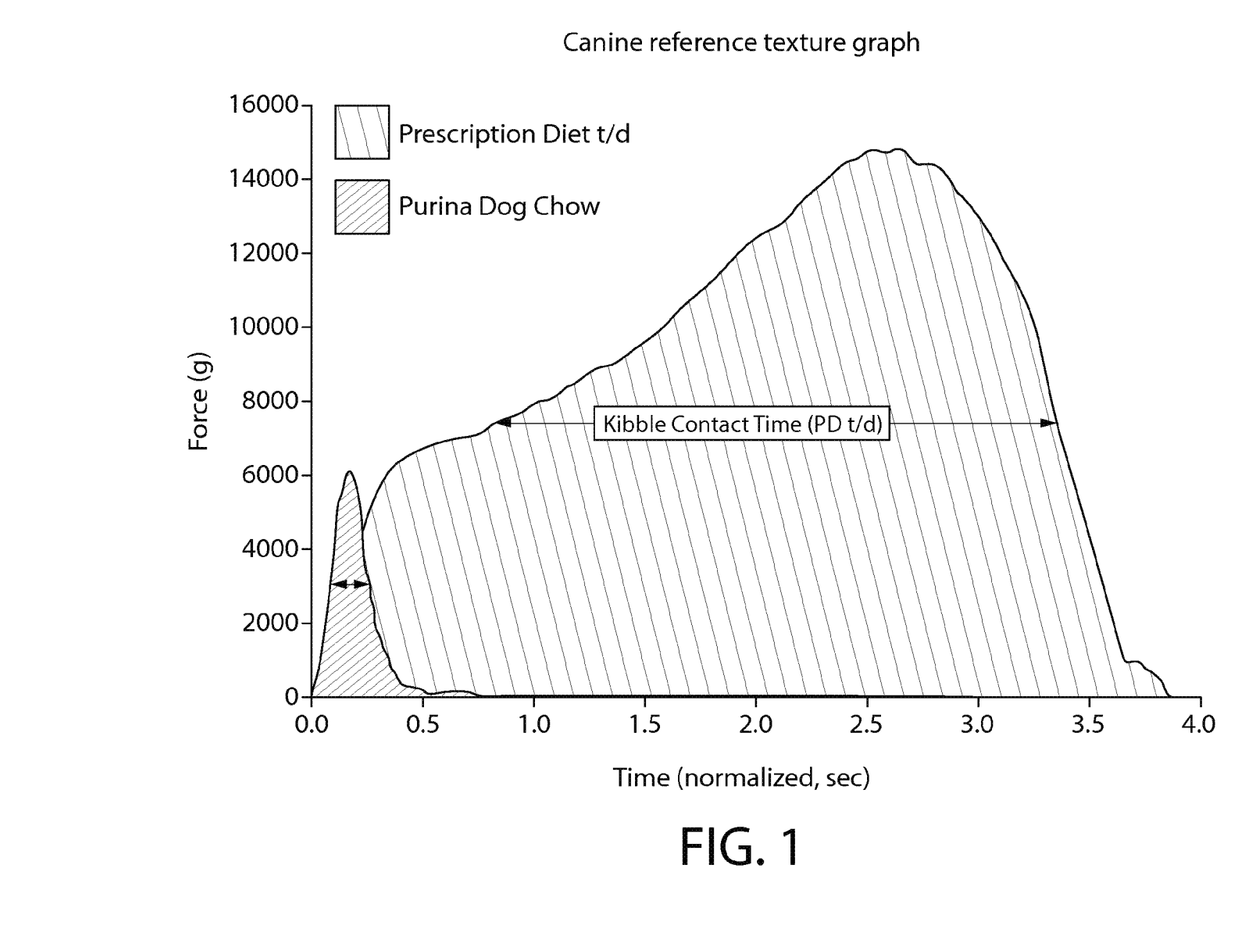
FIG. 1 is a graph depicting contact time for two commercially available dog foods (Hill's® Prescription Diet® t/d® and Purina Dog Chow®) as described in the Examples.
Figure 2:
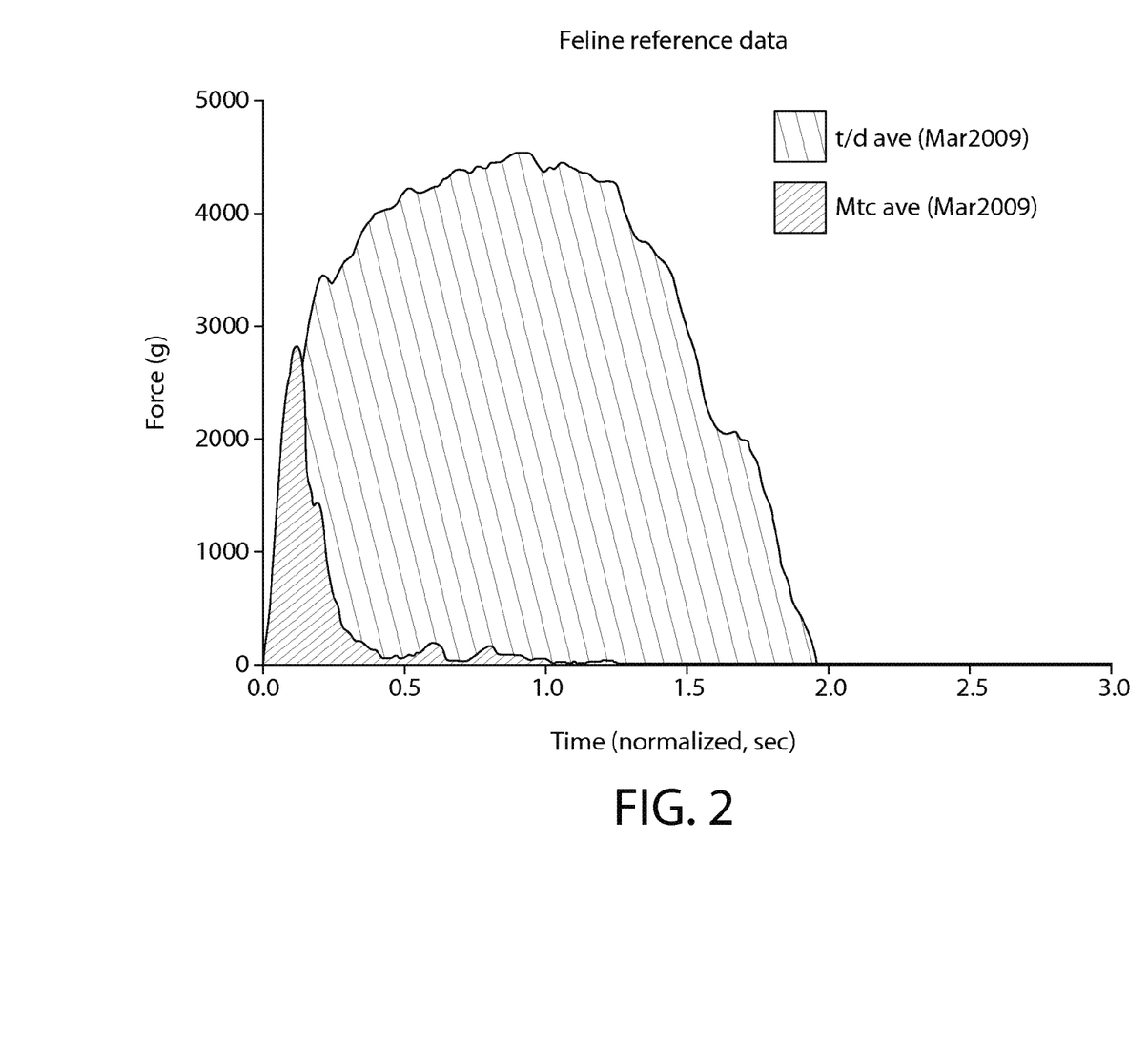
FIG. 2 is a force (g) versus time graph for two commercially available cat foods (Science Diet® Feline Adult Maintenance Food and Hill's® Prescription Diet® t/d® Feline, which is used for dental efficacy).
Figure 3:
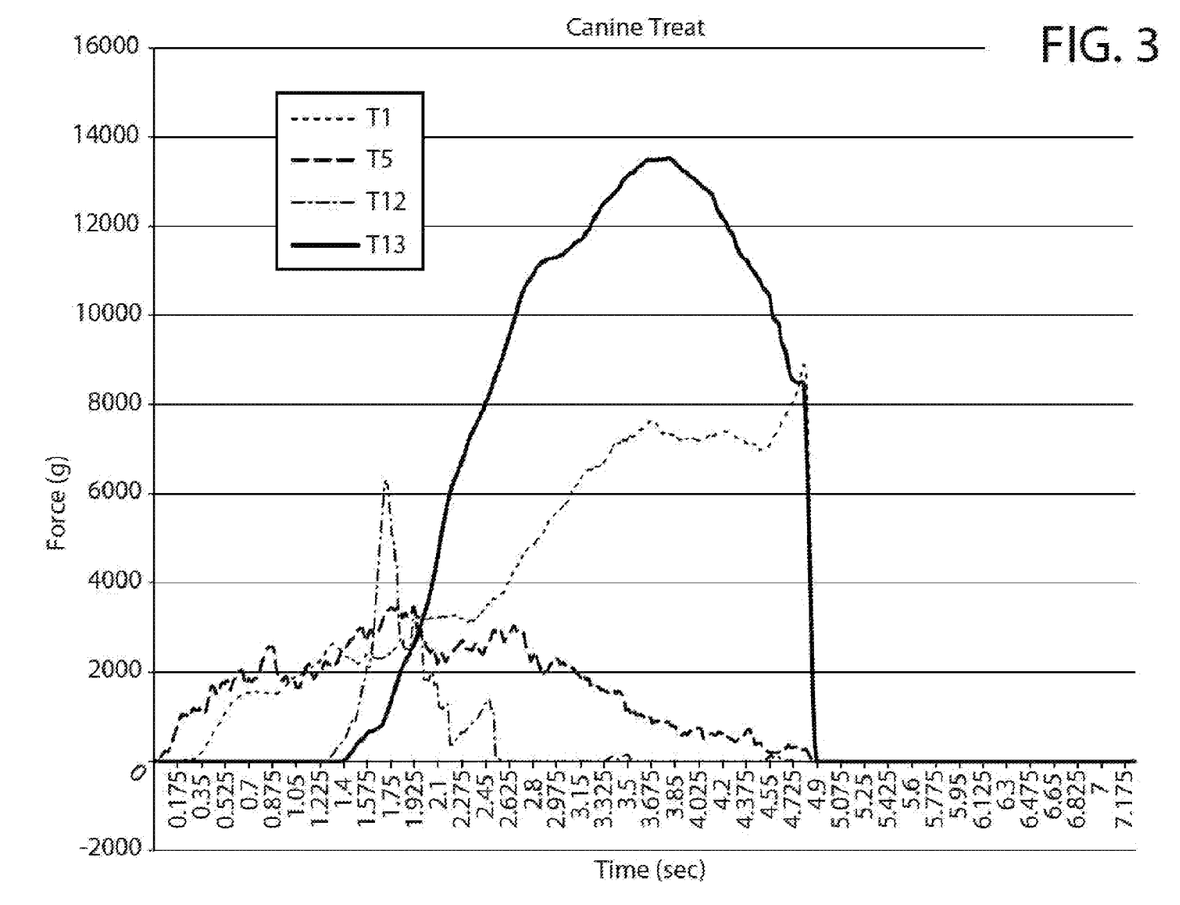
FIG. 3 is a force (g) versus time graph for kibble formulations (T1, T5, T12 and T13) as described in the present Examples.

A graphic illustration of determination of contact time is provided in FIG. 1. FIG. 1 depicts a comparison of contact times between two commercially available dog foods, Hill's® Prescription Diet® t/d®, Canine and Purina Dog Chow®. The contact time is determined at the half force height where the probe is in contact with the kibble. FIG. 2 is a force (g) versus time graph for two commercially available cat foods (Science Diet® Feline Adult Maintenance Food and Hill's® Prescription Diet® t/d® Feline, which is used for dental efficacy). As is evident from FIG. 2, the contact time of the Hill's® Prescription Diet® t/d® Feline is less than the canine diet. See also FIG. 3, which depicts the force versus time graphs for Test ID T1 (conventional product formulation) and Test IDs T5, T12 and T13 according to the present disclosure. As evident from the discussion below, the contact time of the present animal food products are comparable to those of Hill's® Prescription Diet® t/d®, Canine.

Table 4 depicts the dimensions of the kibble (width, length and thickness in millimeters), the distance (millimeters) the probe travels in the kibble before breakage and the percent kibble thickness penetrated before breakage, the contact time (seconds) and the peak force (g) before the kibble begins to crumble. In addition, the average peak force for twenty replicates of each formulation is included in the table.

As indicated in Table 4, the animal food products of the present disclosure are more resistant to breakage than conventional products. For example, when the probe is used to penetrate an animal food product of the present disclosure comprising hydrolyzed protein, the probe is able to penetrate from about 6 mm (29.2%) to about 10 mm (46.6%) of the animal food product in a time period ranging from about 1.30 to about 2.15 seconds before breakage of the present animal food product at about 8.9 kg-force and 11.3 kg-force, respectively. In contrast, the probe is only able to penetrate conventional animal food products, which do not contain hydrolyzed proteins, for a distance of 0.85 mm (4.9%) in 0.17 seconds.

Further efficacy can be achieved by the addition of the high amylopectin content starch, in this case Eliane™ 100 potato starch. As indicated in Table 4, the distance penetrated by the probe and the contact time of the probe can be improved in comparison to hydrolyzed protein alone. For example, the inclusion of 29.50 wt % of high amylopectin content starch and hydrolyzed protein increased the distance penetrated by the probe to 13.450 mm in 2.69 seconds. See Test ID No. T5 in Table 4

Further, as shown in Table 4, the addition of cellulose to the instant animal food product containing hydrolyzed protein and high amylopectin content starch can increase the amount of kg-force required (11.3 kg-force to about 17 kg-force on average) before breaking of the product without a reduction in contact time. As seen in Table 4, the addition of cellulose in combination with the high amylopectin content starch and hydrolyzed protein demonstrated a distance penetrated by the probe of 15.212 mm and 12.640 mm in 3.12 and 2.55 seconds, respectively. See Test ID Nos. T8 and T12. Accordingly, the textural properties of the present animal food product that promote dental efficacy are significantly better than those of standard dried pet food.

TABLE 4

| Test ID | Width (mm) | Length (mm) | Thickness (mm) | Distance to breakage (mm) (percentage of thickness) | Contact Time (seconds) | Peak Force (g) | Average Peak Force (g) SD CV |
|---|---|---|---|---|---|---|---|
| T1 (hydrolyzed protein only) | 31.7 | 23.3 | 77.3 | 10.387 (46.6%) | 2.15 | 8902.35 | 10636.986 1818.373 17.095 |
| T2 (hydrolyzed protein and 3.69% high amylopectin content) | 31.3 | 22.3 | 22.3 | 8.346 (37.4%) | 1.75 | 10460.6 | 10479.101 1828.691 17.451 |
| T3 (hydrolyzed protein and 7.38% high amylopectin content) | 32.7 | 22.4 | 23.5 | 9.962 (42.4%) | 2.06 | 3455.7 | 8107.081 1239.906 15.294 |
| T4 (hydrolyzed protein and 14.75% high amylopectin content) | 24.1 | 23.1 | 24.7 | 10.896 (44.1%) | 2.17 | 3524.405 | 7409.6 1335.642 18.026 |
| T5 (hydrolyzed protein and 29.50% high amylopectin content) | 37 | 25.7 | 18.9 | 13.450 (71.0%) | 2.69 | 3464.085 | 8145.12 2373.758 29.143 |
| T6 (hydrolyzed protein and cellulose) | 30.2 | 27 | 20.7 | 6.045 (29.2%) | 1.30 | 11334.95 | 11367.287 1767.683 15.551 |
| T7 (hydrolyzed protein, 3.44% high amylopectin content and cellulose) | 30.9 | 24.5 | 22.2 | 13.812 (62.2%) | 2.79 | 8767.825 | 11706.912 2077.742 17.748 |
| T8 (hydrolyzed protein, 6.88% high amylopectin content and cellulose) | 30.5 | 25.4 | 21.6 | 15.212 (70.4%) | 3.12 | 8498.595 | 11350.107 2419.685 21.319 |
| T9 (hydrolyzed protein, 13.75% high amylopectin content and cellulose) | 30.9 | 26.9 | 21.3 | 8.366 (39.3%) | 1.78 | 10397.23 | 11475.428 2372.254 20.672 |
| T10 (hydrolyzed protein, 27.5% high amylopectin content and cellulose) | 30.3 | 27.3 | 19.7 | 6.170 (31.3%) | 1.34 | 12649.75 | 12812.925 1732.382 13.521 |
| T11 (hydrolyzed protein, 59% high amylopectin content) | 30.4 | 17.2 | 17.6 | 9.500 (54%) | 1.90 | 9426.08 | 17563.375 4398.054 25.041 |
| T12 (hydrolyzed protein, 55% high amylopectin content and cellulose) | 27.1 | 26 | 17 | 12.640 (74.3%) | 2.55 | 13528.16 | 16143.565 1962.356 12.156 |

TABLE 4-continued

| Test ID | Width (mm) | Length (mm) | Thickness (mm) | Distance to breakage (mm) (percentage of thickness) | Contact Time (seconds) | Peak Force (g) | Average Peak Force (g) SD CV |
|---|---|---|---|---|---|---|---|
| T13 (high amylopectin content only) | 23.4 | 21.2 | 17.2 | 0.850 (4.9%) | 0.17 | 6208.775 | 14834.193 3990.404 26.9 |

What is claimed is:

1. An animal food product for promoting dental efficacy comprising:
   20 wt % to 60 wt % of a hydrolyzed protein comprising one or more amino groups, and
   a high amylopectin content starch comprising an amylopectin content of at least 99% and reducing sugars, wherein the reducing sugars are present in an amount of 0.5% to 20% dry weight based on the weight of the high amylopectin content starch;
   wherein the one or more amino groups in the hydrolyzed protein are covalently bonded to the reducing sugars of the high amylopectin content starch, and
   wherein the reducing sugars of the high amylopectin content starch comprise free aldehydes, and wherein the free aldehydes covalently bond the reducing sugars to the one or more amino groups in the hydrolyzed protein.

2. The animal food product of claim 1, further comprising fiber, wherein the fiber is cellulose.

3. The animal food product of claim 1, wherein the animal food product is formed and textured such that a probe having a contact area of about 6.80 mm wide×1.00 mm thick operated at a speed of about 5 mm/s penetrates the animal food product for at distance of at least 50% of the thickness of the animal food product prior to breaking the animal food product, wherein the probe contacts the animal food product for at least about 2.5 seconds prior to breaking the animal food product.

4. The animal food product of claim 1, wherein a force for breaking the animal food product exerted by a probe having a contact area of about 6.80 mm wide×1.00 mm thick ranges from about 8 kg-force to 12 kg-force.

5. The animal food product of claim 1, wherein the animal food product is a kibble, wherein the kibble is in the form of at least one shape selected from the group consisting of a tube, a triangle, a sphere, a cross and a disc.

6. The animal food product of claim 1, wherein the animal food product is a selected from the group consisting of a supplement, a treat and a toy.

7. The animal food product of claim 1, wherein the high amylopectin content starch is selected from the group consisting of a waxy maize starch, a waxy rice starch, a waxy barley starch, a waxy sorghum starch, a waxy wheat starch and a waxy potato starch.

8. The animal food product of claim 1, wherein the high amylopectin content starch is a waxy potato starch.

9. The animal food product of claim 1, wherein the hydrolyzed protein comprises a protein hydrolysate having a molar mass distribution ranging from 8,000 to 10,000 daltons.

10. The animal food product of claim 1, further comprising a common starch having an amylose content of about 25%.

11. The animal food product of claim 1, further comprising at least one antioxidant selected from the group consisting of vitamin C, vitamin E, vitamin A, lipoic acid, astaxanthin, beta-carotene, L-carnitine, coenzyme Q10, glutathione, lycopene, lutein, N-acetylcysteine, soy isoflavones, S-adenosylmethionine, taurine, tocotrienols, spinach, tomato, citrus fruit, grape, carrot, broccoli, green tea, *Ginkgo biloba*, corn gluten meal, rice bran, algae, curcumin, marine oil, fruits, vegetables, yeast, carotenoids, flavonoids, polyphenols, and mixtures thereof.

12. The animal food product of claim 1, wherein the hydrolyzed protein is present in an amount of 35 wt % to 40 wt %.

13. The animal food product of claim 1, wherein the hydrolyzed protein is present in an amount of 37 wt % to 39 wt %.

14. The animal food product of claim 1, wherein the high amylopectin content starch comprises the reducing sugars in an amount of 0.5% to 10% dry weight based on the weight of the high amylopectin content starch.

15. The animal food product of claim 1, wherein the high amylopectin content starch comprises the reducing sugars in an amount of 0.5% to 5% dry weight based on the weight of the high amylopectin content starch.

16. The animal food product of claim 1, wherein the animal food product is a nutritionally incomplete food.

17. The animal food product of claim 16, further comprising fiber and a common starch, wherein the fiber is cellulose, and wherein the hydrolyzed protein comprises a protein hydrolysate having a molar mass distribution ranging from 8,000 to 10,000 daltons, and wherein the common starch comprises an amylose content of about 25%.

18. The animal food product of claim 1, wherein:
   the hydrolyzed protein is present in an amount of 37 wt % to 39 wt %; and
   the high amylopectin content starch comprises the reducing sugars in an amount of 0.5% to 5% dry weight based on the weight of the high amylopectin content starch.

19. A method of preparing the animal food product of claim 1 for promoting dental efficacy, the method comprising:
   preparing a food mixture comprising the high amylopectin content starch and the hydrolyzed protein;
   working the food mixture under mechanical pressure and heat sufficient to convert the mixture to a flowable mass; and
   discharging the flowable mass through a die to form an extrudate comprising the high amylopectin content starch and the hydrolyzed protein.

20. A method of promoting dental efficacy in an animal, the method comprising:
   feeding the animal food product of claim 1 to an animal in need thereof.

\* \* \* \* \*